United States Patent [19]

Gatzke

[11] 4,147,162

[45] Apr. 3, 1979

[54] DEFIBRILLATOR MONITOR BASELINE CONTROL

[75] Inventor: Ronald D. Gatzke, Lexington, Mass.

[73] Assignee: Hewlett-Packard Company, Palo Alto, Calif.

[21] Appl. No.: 805,550

[22] Filed: Jun. 10, 1977

[51] Int. Cl.² ................................. A61R 5/04
[52] U.S. Cl. ..................... 128/2.06 B; 128/419 D
[58] Field of Search ............ 128/2.06 B, 2.1 P, 419 D

[56] References Cited

U.S. PATENT DOCUMENTS

| | | | |
|---|---|---|---|
| 3,534,282 | 10/1970 | Day | 128/2.06 B |
| 3,547,108 | 12/1970 | Seiffert | 128/419 D |
| 3,569,852 | 3/1971 | Berkovits | 128/2.06 B |
| 3,653,387 | 4/1972 | Ceier | 128/419 D |
| 3,991,748 | 11/1976 | Ohlsson | 128/2.06 B |

Primary Examiner—William E. Kamm
Attorney, Agent, or Firm—Donald N. Timbie

[57] ABSTRACT

In order to lessen the time that the baseline of an oscilloscope is driven off scale after the discharge through the paddles of a defibrillator, means are provided for attenuating the low frequencies in the signals applied to the output amplifier for a short time after the discharge pulse is initiated.

2 Claims, 3 Drawing Figures

DEFIBRILLATOR MONITOR BASELINE CONTROL

BACKGROUND OF THE INVENTION

When the heart goes into a state of fibrillation its muscles contract in a random manner so that it cannot pump blood, but it can often be made to resume normal synchronous operation by passing a pulse of current through it. This is done by a defibrillator that discharges a storage capacitor through paddle electrodes that are pressed against certain locations on the patient's chest. As each discharge may do some damage to the heart, it is desirable to known when it has resumed normal operation. For this reason cardiographic signals are derived either from the paddle electrodes or a set of ECG electrodes and applied to form a cardiographic waveform on an oscilloscope or other display device. If the signals for the oscillocope are being derived from the paddle electrodes, it takes approximately five seconds after discharge for the voltage between them to return to zero. For most of this time the voltage is more than enough to drive the baseline for the electron beam of the oscilloscope off scale so that no waveforms can be seen. If the signals are derived from ECG electrodes of poor quality the same thing occurs. Between about one and one-half and three seconds after the discharge of the defibrillator, the heart may exhibit a few transitory beats and then revert to a condition of fibrillation. This generally means that further defibrillation discharges may be futile and that other methods such as the injection of chemicals are required in order to revive the patient. Under the condition described where no waveform appears on the oscilloscope for nearly five seconds, these transitory heart beats cannot be observed so that additional pulses of current are passed through the heart by the defibrillator. By the time it is realized that chemical methods must be used, it may well be too late.

BRIEF DESCRIPTION OF THE INVENTION

Analysis of the discharge recovery waveform of the paddle electrodes, or of the ECG electrodes, reveals that a major portion of the energy lies in a low frequency region. Therefore, if the discharge signals from the paddles or ECG electrodes is passed through a filter that attenuates these low frequencies, the voltage applied to the oscilloscope can be so reduced that the baseline remains in view for most of the five second period after discharge. This permits a transitory cardiographic wave that would otherwise not be in view to be seen. After a few seconds the characteristic of the filter is restored to its former state so as to permit a more accurate waveform to be reproduced. However, this temporary loss in fidelity of the waveform is to be preferred to the total loss of the waveform that occurs without the invention. The filter can be controlled by the discharge pulse from the paddles or by a switch operated simultaneously with the manual discharge switch.

DESCRIPTION OF AN EMBODIMENT

Figure 1:
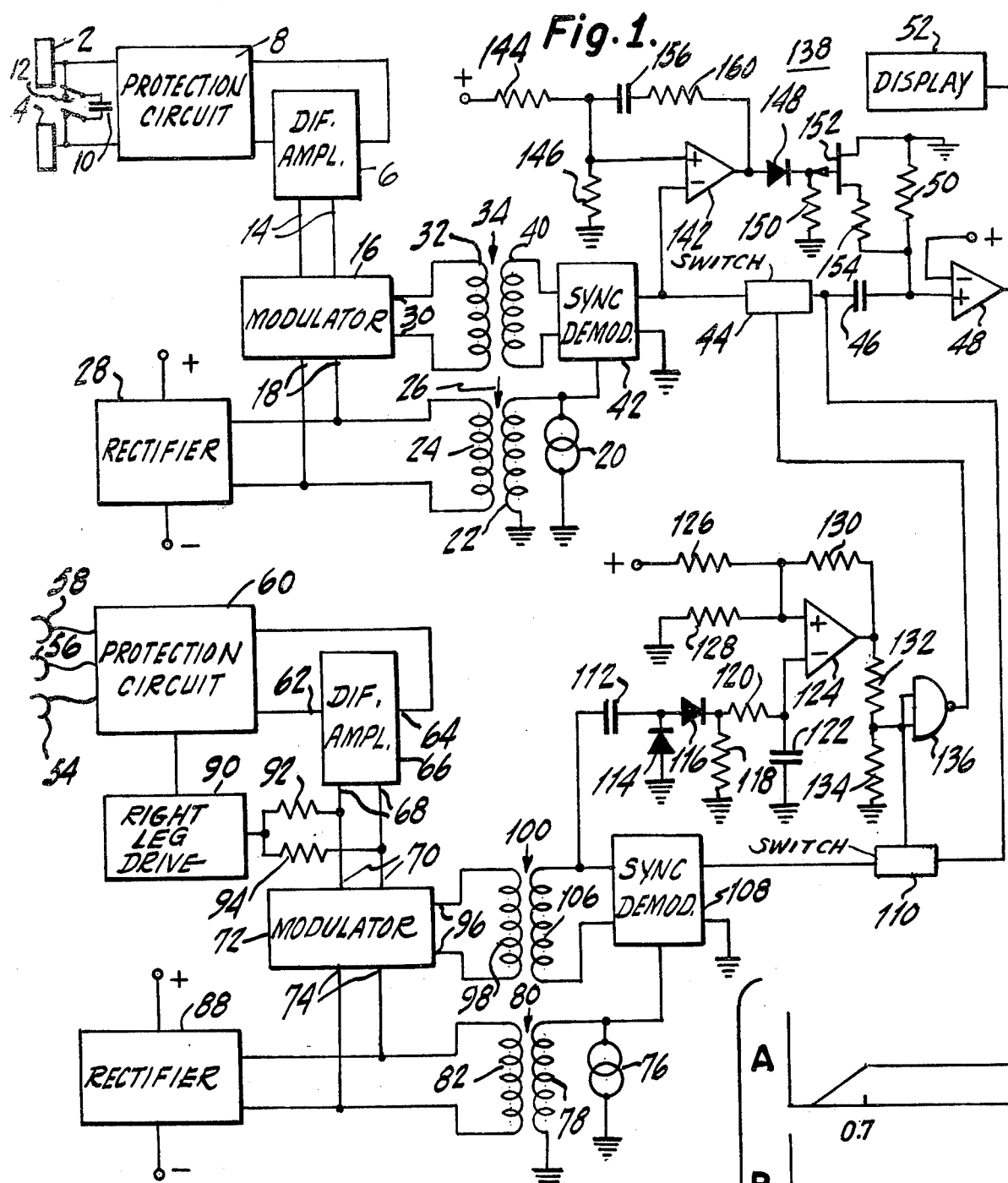
FIG. 1 is a schematic diagram of one embodiment of the invention.
Figure 3:
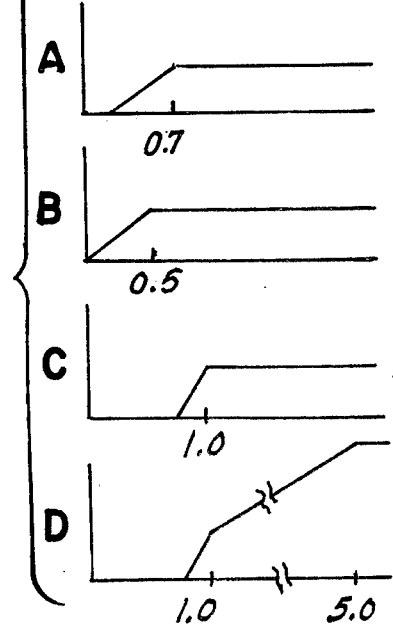
FIG. 3 illustrates the frequency characteristics of filters shown in FIG. 1.

In the drawing, paddle electrodes 2 and 4 are coupled to a differential amplifier 6 via circuit 8 that protects the amplifier from the high voltages occurring when a storage capacitor 10 is discharged through the body of the patient via the paddles 2 and 4 by closure of a switch 12. The output circuit of the amplifier 6 has a roll off below 0.7 of a cycle of 6 db/octave as shown in FIG. 3A and is coupled to an input 14 of a modulator 16 so as to modulate the amplitude of a carrier wave that is applied to another input 18. The carrier wave is derived from a source 20 via the primary winding 22 and secondary winding 24 of a transformer 26. Operating potentials for the differential amplifier 6 and the modulator 16 are derived by rectifying the carrier wave at the secondary winding 24 with a rectifier 28.

The modulated carrier wave appearing at the output 30 of the modulator 16 is applied across a primary winding 32 of a transformer 34 having a secondary winding 40 coupled to a synchronous demodulator 42. The other input of the synchronous demodulator 42 is coupled to the source 20 of carrier waves so as to synchronously detect the amplitude modulation of the output signals from the modulator 16. A normally open switch 44 is connected in series with a capacitor 46 between the output of the demodulator 42 and the noninverting input of an output amplifier 48. A resistor 50 is connected between this input and the ground. The capacitor 46 and the resistor 50 provide a 6 db/octave roll off in frequency below 0.5 cycles as indicated in FIG. 3B. The output of the amplifier 48 is applied to a display means 52 for forming an image of the cardiographic waveform.

Because the quality of the cardiographic signals provided by the paddles 2 and 4 is less than that desired, it may be arranged to apply cardiographic signals to the amplifier 48 from ECG electrodes 54, 56 and 58 for the right leg, left arm and right arm if these electrodes are properly attached. The electrodes are coupled via protection circuits 60 to the inputs 62 and 64 of a differential amplifier 66. The output 68 of the amplifier 66 is coupled to one input 70 of a modulator 72 so as to modulate the amplitude of a carrier wave applied to another input 74. The carrier wave is supplied by a source 76 that is connected across the primary winding 78 of a transformer 80 and the ends of the secondary winding 82 are connected to the input 74. Operating potential for the amplifier 66 and the modulator 72 are derived by coupling a rectifier 88 to the secondary winding 82.

A right leg drive circuit 90 may be provided for causing the reference or guard potential for the floating circuits to track variations in potential produced in the body of the patient by lights, electric cables, etc. and thereby eliminate the effect that these variations in potential would have on the desired output signals. It is controlled by the average voltage at the output 68 of the amplifier 66 by connecting its input to the junction of resistors 92 and 94 that are connected in series across the output 68. The output of the drive circuit 90 is connected to the right leg electrode 54 via the protection circuits 60.

The amplitude modulated carrier wave at the output 96 of the modulator 72 is applied across a primary winding 98 of a transformer 100. The secondary winding 106 of the transformer 100 is coupled to a synchronous demodulator 108 wherein the output of the modulator 72 is mixed with the carrier wave applied to another input from the source 76 and thus produce the detected amplitude modulation at the output. A normally closed switch 110 is connected between the output of the synchronous demodulator 108 and the side of the capacitor 46 that is remote from the noninverting input of the output amplifier 48.

In a manner explained in a copending application bearing Ser. No. 805,552 and filed concurrently herewith in the names of myself and Dana C. Finlayson, Robert Stettiner, the switch 44 remains normally open and the switch 110 normally closed unless at least one of the ECG leads 54, 56 or 58 falls off or becomes maladjusted. When this happens, the positions of the switches are reversed so that the switch 44 is closed and the switch 110 opened causing the output amplifier 48 to receive the cardiographic signals from the paddles 2 and 4 rather than from the ECG electrodes 56 and 58. In this case the combined roll off provided by the output circuit of the amplifier 6 and the input circuit of the amplifier 48 is 12 db/octave below a frequency of one cycle as shown in FIG. 3C. The means by which the switching is effected does not form part of the invention, but as shown, it includes a capacitor 112 coupled in series with a diode 114 between one end of the secondary winding 106 and ground, a series circuit of a diode 116 and a resistor 118 connected in parallel with the diode 114 and a series circuit for providing delay comprised of a resistor 120 and a capacitor 122 connected in parallel with the resistor 118. The junction of the resistor 120 and the capacitor 122 is connected to the inverting input of an amplifier 124. Resistors 126 and 128 are connected in series between a point of positive potential and ground and their junction is connected to the noninverting input of the amplifier 124. A resistor 130 is connected between the noninverting input and the output of the amplifier 124, and resistors 132 and 134 are connected in series between the output and ground. Their junction is connected to the input of an inverter 136 and to the switch 110, and the output of the inverter 136 is connected to the switch 44.

When the ECG electrodes 54, 56 and 58 are properly attached to the patient, the rectified voltage produced at the inverting input of the amplifier 124 is less than the voltage applied to its noninverting input from the junction of the resistors 126 and 128 so that the voltage applied to the switch 110 and the input of the inverter 136 is positive. This keeps the switch 110 closed and the switch 44 open.

As explained more fully in the above identified application, whenever one of the electrodes 54, 56 or 58 falls off, the modulated signal increases in amplitude to such an extent that the rectified voltage applied to the inverting terminal of the amplifier 124 becomes larger than the voltage applied to its noninverting input. The output of the amplifier 124 then becomes negative so as to open the switch 110 and close the switch 44.

The Invention

Figure 2:
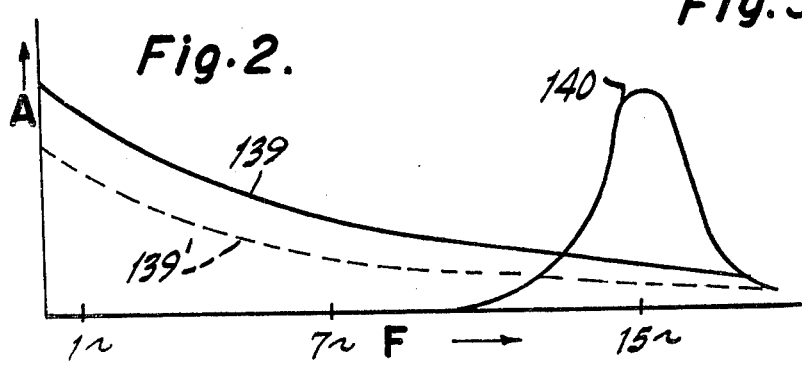
FIG. 2 is a graphical representation of the energy distribution with frequency of the discharge waveforms of the paddles and of a normal heart cycle.

Whether the cardiographic signals are derived from the paddles 2 and 4 or from the ECG electrodes 54 and 56, the circuit 138 operates to attenuate more low frequencies by reducing the time constant of the input circuit of the amplifier 48, but before considering the circuit in detail reference is made to the graphs of FIG. 2. The graphs 139 and 139' illustrate the distribution of the energy of the recovery waveform of the paddles 2 and 4 with frequency at respectively successive times following the defibrillation pulse, and the graph 140 illustrates the distribution of the energy of a cardiographic waveform with frequency. When the heart is in fibrillation, the energy distribution lies between one and seven cycles.

The defibrillator pulse produces signals of very large amplitude between the inputs of the differential amplifier 6 so that the output of the synchronous demodulator 42 is also very large. In accordance with the invention, means are provided for responding to this condition to attenuate the low frequencies applied to the amplifier 48. In this particular embodiment this is accomplished by connecting the inverting input of a comparator 142 to the output of the synchronous demodulator 42 and connecting the noninverting input to a junction of resistors 144 and 146 that are connected between a point of positive potential and ground. The output of the comparator 142 is connected to a diode 148 and a resistor 150, and the voltage across the resistor 150 is applied to the gate electrode of a FET 152. The source-drain path of the FET 152 is connected in series with a limiting resistor 154, and the series circuit thus formed is connected in shunt with the resistor 50.

When a defibrillator pulse is not present, the voltage at the noninverting input of the comparator 142 is greater than the voltage at the inverting input so that the output of the comparator is positive. This produces a positive voltage at the gate of the FET 152 so as to cause it to be turned off. But when a defibrillator pulse occurs, the voltage between the paddles 2 and 4 is very large so as to cause the output voltage of the amplifier 6 to be large. As a consequence, the amplitude of the signal at the output of the synchronous demodulator 42 becomes larger than the voltage applied to the noninverting terminal of the comparator 142. Its output becomes negative so as to cut off the diode 148 and remove the bias from the gate of the FET 152. The source to drain impedance of the FET 152 becomes nearly zero so that the resistor 154 is effectively in shunt with the resistor 50. Because the resistance of the resistor 154 is much smaller than the resistance of the resistor 50, the RC time constant of the input circuit for the amplifier 48 is reduced so as to cause its response to roll off at 6 db per octave rate for frequencies below a higher predetermined frequency such as 5 cycles and to roll off at a 12 db/octave rate for frequencies below one cycle as illustrated in FIG. 3D. If the switch 44 is closed so that the paddles 2 and 4 are being used to provide cardiographic signals to the output amplifier 48, most of the discharge voltage from the paddles is prevented from reaching the amplifier 48 so that the baseline of an oscilloscope coupled to the output of the amplifier 48 is not moved off scale. At the same time, however, the higher frequency energy of the cardiographic waveforms is permitted to reach the amplifier 48. After a second or so, as determined by the values of the capacitor 156 and a resistor 160 that are connected in series between the output of the comparator 142 and its noninverting input, the voltage at the output of the comparator 142 returns to a positive value so as to cut off current flow between the source and drain electrodes of the FET 152 and restore the time constant of the input circuit of the amplifier 48 to its former value. This is necessary in order to produce cardiographic signals of better quality that may be required for synchronous operation. Even if the waveforms produced within a few seconds after discharge are not of the best quality, it is better to be able to see them than not to see them at all.

If the cardiographic signals applied to the amplifier 48 are derived from the ECG electrodes 56 and 58 and if they are of inferior quality, the circuit 138 will prevent the low frequency energy derived from them from deflecting the baseline of the oscilloscope off scale.

The embodiment of the invention just described is intended for use in a defibrillator that is powered by power systems that are referenced to ground so as to require preamplifiers 6 and 66 but it can be used in a battery powered defibrillator having only one amplifier as it is still important to prevent the baseline of the oscilloscope employed from going off scale in response to the defibrillation pulse. This can be done by attenuating the low frequencies prior to their application to the oscilloscope for a short time after the defibrillator pulse occurs.

What is claimed is:

1. Apparatus for use with a defibrillator monitor, comprising the combination of
    a pair of electrodes for application to a patient's body so as to derive cardiographic signals therefrom,
    an amplifier having an input and an output, and
    means coupled to said electrodes for increasing the attenuation of low frequency energy passing through said amplifier for a predetermined interval following the occurrence of a signal that is in excess of a predetermined amplitude and which is derived from said electrodes prior to its application to the input of said means for increasing the attenuation of low frequency energy.

2. A circuit for coupling ECG signals from a pair of electrodes of a defibrillator to the input of a monitor in such manner that the display of the ECG signals on the monitor will not be driven off scale by the presence of a pulse on said electrodes exceeding a given amplitude and having a large portion of its energy within the lower frequencies contained in an ECG signal, comprising
    an input to which said electrodes may be coupled,
    an output for coupling to a monitor,
    a filter coupled between said input and said output, said filter passing both the low and high frequencies contained within the ECG signal,
    means coupled to said filter for increasing its attenuation for the lower frequencies of the ECG signal, and
    means causing said latter means to attenuate the low frequencies for an interval of time following the appearance of a pulse at said input that exceeds a given amplitude.

* * * * *